United States Patent
Magnussson et al.

(10) Patent No.: US 6,540,731 B2
(45) Date of Patent: Apr. 1, 2003

(54) ABSORBENT ARTICLE PROVIDED WITH A BELT

(75) Inventors: Ing-Britt Magnussson, Oxelvägen (SE); Pia Loft, Vilshärads Rapsväg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/847,412

(22) Filed: May 3, 2001

(65) Prior Publication Data

US 2002/0019620 A1 Feb. 14, 2002

Related U.S. Application Data

(63) Continuation of application No. PCT/SE99/01975, filed on Nov. 3, 1999.

(30) Foreign Application Priority Data

Nov. 6, 1998 (SE) .............................. 9803803

(51) Int. Cl.⁷ ............................... A61F 13/15
(52) U.S. Cl. ..................................... 604/392
(58) Field of Search ................... 604/386, 387, 604/392, 396

(56) References Cited

U.S. PATENT DOCUMENTS 5,706,524 A    1/1998   Herrin et al.

FOREIGN PATENT DOCUMENTS

| EP | 0 287 388    | 10/1988 |
| EP | 0 409 307    | 1/1991  |
| EP | 0 418 493    | 3/1991  |
| EP | 0 486 006 A2 | 5/1992  |
| EP | 0 605 012    | 7/1994  |
| FR | 2 586 558    | 3/1987  |
| TW | 233473       | 11/1994 |
| WO | 97/34037     | 9/1997  |
| WO | 98/37847     | 9/1998  |

OTHER PUBLICATIONS

Sueo Kawabata, "The Standardization and Analysis of Hand Evaluation", Second Edition, The Hand Evaluation and Standardization Committee, The Textile Machinery Society of Japan, published by The Textile Machinery Society of Japan, Osaka, Japan, Jul. 1980.

Primary Examiner—Dennis Ruhl
(74) Attorney, Agent, or Firm—Burns, Doane, Swecker & Mathis, L.L.P.

(57) ABSTRACT

Absorbent article such as a diaper and an incontinence guard having a liquid permeable topsheet (2), a liquid impermeable backsheet (3) and an absorbent body (4) enclosed therebetween, the article having a front portion (5), a rear portion (6) and a crotch portion (7) therebetween, and further is provided with a belt (9) attached to or intended to be attached to the rear portion (6) of the article and to the front portion (5) of the article, in such a way that the article will assume a pantlike shape, where the belt (9) forms a part of the waist portion of the pant. In order to avoid skin injuries and irritations the belt (9) includes a flexible laminate of a carrier material (11) intended to form the outside of the belt and a nonwoven material (12) forming the inside of the belt which will be in direct contact with the user, the laminate has a Shinyakasa value according to Kawabata of 5 or more.

9 Claims, 2 Drawing Sheets

ABSORBENT ARTICLE PROVIDED WITH A BELT

This is a continuation of PCT/SE99/01975, filed Nov. 3, 1999.

TECHNICAL FIELD

The present invention refers to an absorbent article such as a diaper and an incontinence guard comprising a liquid permeable topsheet, a liquid impermeable backsheet and an absorbent body enclosed therebetween, said article having a front portion, a rear portion and a crotch portion therebetween, and further is provided with a belt attached to or intended to be attached to the rear portion of the article and to the front portion of the article, in such a way that the article will assume a pantlike shape, where the belt forms a part of the waist portion of the pant.

BACKGROUND OF THE INVENTION

Diapers and incontinence guards for incontinent adults usually have a garment portion holding an absorbent body in place against the user's body and attachment means which hold the garment portion in place also when the user is moving. A common type of attachment means are adhesive tapes or hook and loop fasteners of the touch-and-close type which directly attach the front and rear portions of the absorbent article to each other. It is further known, through e g WO 98/37847, EP-A-0 287 388, EP-A-0 409 307, EP-A-0 605 012 and FR-A-2 586 558, to attach the front and rear portions of the article by means of a belt, at which the possibilities to adjust the fit are improved.

A problem with these belts is that they easily cause skin irritations to the user, due to that the belt is in direct contact with the skin of the wearer and has to be tightened relatively strongly in order to have a satisfactory fit and security against leakage of the diaper or incontinence guard. By the tight contact and friction between the belt and the skin there will be a mechanic wear of the skin which gives rise to irritation and even skin injuries.

THE OBJECT AND MOST IMPORTANT FEATURES OF THE INVENTION

The object of the invention is to provide a belt for absorbent articles which is kind to the skin and by that does not give rise to skin irritations and injuries. This has been solved by the fact that the belt comprises a flexible laminate of a carrier material intended to form the outside of the belt and a soft nonwoven material intended to form the inside of the belt and which will be in contact with the skin of the user, at which said laminate has a Shinyakasa value according to Kawabata of 5 or more.

The test method in question is used in the textile industry for measuring smoothness and flexibility of a material and is disclosed in "The Standardization and Analysis of Hand Evaluation (2 nd Edition), Sueo Kawabata, July 1980, The Hand Evaluation and Standardization Committee, The Textile Machinery Society of Japan", a copy of which has been filed in this application.

Other features of the invention are disclosed in the following description and claims.

DESCRIPTION OF DRAWINGS

The invention will in the following be closer described with reference to an embodiment shown in the accompanying drawings.

DESCRIPTION OF AN EMBODIMENT

Figure 1:
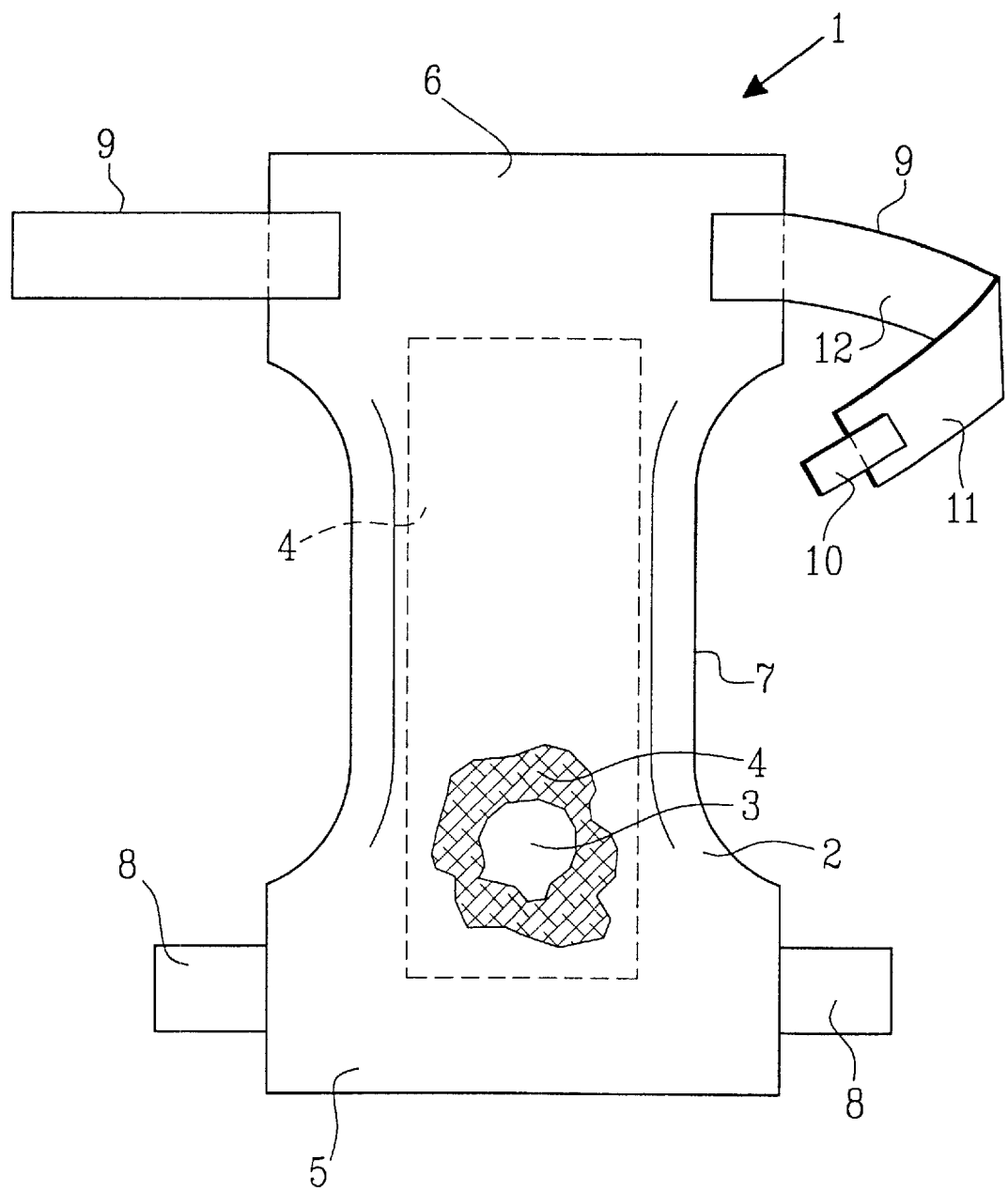
FIG. 1 shows schematically a plan view of an absorbent article according to the invention.

The drawing shows an embodiment of a diaper or incontinence guard 1 comprising a liquid permeable topsheet 2, a liquid impermeable backsheet 3 and an absorbent body 4 enclosed therebetween. The liquid permeable topsheet 2 can consist of a nonwoven material, e g a spunbond material of continuous filaments, a meltblown material or a bonded carded fibrous web. The liquid impermeable backsheet 3 may consist of a plastic film, a nonwoven material coated with a liquid impervious material or a hydrophobic nonwoven material which resists liquid penetration.

The topsheet 2 and the backsheet 3 have a somewhat greater extension in the plane than the absorbent body 4 and extends outside the edges thereof. The topsheet 2 and the backsheet 3 are connected to each other within the projecting portions thereof, e.g., by gluing or welding by heat or ultrasonic.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well-known to the person skilled in the art and does therefore not have to be described in detail. The thin absorbent bodies which are common in for example baby diapers and incontinence guards often comprise a compressed mixed or layered structure of cellulosic fluff pulp and superabsorbent.

The diaper is intended to enclose the lower part of the wearer's trunk like a pair of absorbent pants. It comprises a front portion 5 intended during use to be worn on the front part of the user's body, a rear portion 6 intended during use to be worn the rear part of the user's body, and a more narrow crotch portion 7 located between the front and rear portions and which is intended to be worn in the crotch part of the user between the legs. The front portion 5 is provided with a pair of adhesive tape portions 8 or other type of attachment means such as hooks and loops fasteners of the touch and close type, hooks etc.

A pair of belt portions 9 are with one end attached, e.g., glued or ultrasonically welded to the rear part 6 of the diaper. The belt portions 9 are with their opposite ends intended to be fastened together, e.g., by a tape portion 10 which is attached to the outside of the opposite belt portion. Instead of tape there may be another type of optional attachment means, such as hook and loop fasteners, hooks etc. The tape portions 8 or corresponding attachment means of the front portion 5 are intended to be attached against the outside of the belt portion 9 in order to fasten together the diaper to the desired pantlike shape.

The belt portions 9 consist of a laminate of a carrier material 11 forming the outside of the belt, and a soft nonwoven material 12 forming the inside of the belt, which is intended to be in direct contact with the skin of the wearer. In order to avoid skin irritations from the belt the laminate should have a Shinyakasa value according to Kawabata of 5 or more. As mentioned above this is a method used within the textile industry to measure smoothness and flexibility and it is disclosed in the literature.

The Shinyakasa value can be calculated from the following equation:

$$Y = C_0 + \sum_{i=1}^{16} C_i \frac{X_i - \overline{X}_i}{\sigma_i}$$

where:

Y Shinyakasa hand value $X_i$=the $i^{th}$ characteristic value or its logarithm
and $\sigma_i$ are the mean value $\overline{X}_i$ and the standard deviation of the $i^{th}$
characteristic value $C_0$ and Ci are parameters (constant coefficient)

The order of $X_i$ corresponding to i=1, 2, . . . is not common for all the equations, because this follows in order of importance of blocks and also of characteristic values in their blocks to each primary hand. The designation of the blocks (1,2,3 . . . , 6) and the characteristic value $X_i$ (i=0, 1, 2, . . . , 16) are given in Table 1.

TABLE 1

| Block | i | $X_i$ | $\overline{X}_i$ | $\sigma_i$ |
|---|---|---|---|---|
|  | 0 |  |  |  |
| 1 | 1 | LT | 0.5906 | 0.0939 |
|  | 2 | log WT | 1.0551 | 0.2728 |
|  | 3 | RT | 43.6828 | 12.0448 |
| 2 | 4 | log B | −1.7749 | 0.3592 |
|  | 5 | log 2HB | −2.0351 | 0.5126 |
| 3 | 6 | log G | −0.3731 | 0.3044 |
|  | 7 | log 2HG | −0.2733 | 0.5586 |
|  | 8 | log 2HG5 | 0.0295 | 0.4506 |
| 4 | 9 | LC | 0.4483 | 0.1109 |
|  | 10 | log WC | −0.9951 | 0.3174 |
|  | 11 | RC | 49.4168 | 11.6778 |
| 5 | 12 | MIU | 0.2258 | 0.0452 |
|  | 13 | log MMD | −1.6832 | 0.2191 |
|  | 14 | log SMD | 0.4892 | 0.3999 |
| 6 | 15 | log T | −0.4253 | 0.2209 |
|  | 16 | log W | 0.9623 | 0.1768 |

Also, the parameter $C_i$ and the order of the characteristic values for calculating Shinyakasa are given in Table 2.

TABLE 2

| | SHINYAKASA | |
|---|---|---|
| i | $C_i$ | R |
| 0 | 5.3474 |  |
| 4 | −1.6807 | 0.821 |
| 5 | −0.2870 | 0.839 |
| 13 | −0.3788 | 0.862 |
| 14 | 0.2827 | 0.869 |
| 12 | 0.0648 | 0.869 |
| 6 | −0.3688 | 0.895 |
| 7 | −0.0826 | 0.898 |
| 8 | 0.0784 | 0.896 |
| 1 | −0.1810 | 0.898 |
| 3 | 0.0795 | 0.899 |
| 2 | −0.0263 | 0.899 |
| 9 | −0.0203 | 0.898 |
| 10 | 0.1411 | 0.898 |
| 11 | −0.0382 | 0.897 |
| 16 | 0.1019 | 0.897 |
| 15 | −0.0534 | 0.898 |

Note:
log means $\log_{10}$; Each of the characteristic values which belongs to blocks 1, 2, 3 and 5 is the mean value of those of warp and weft directions. After mean value is calculated from the characteristic values of both directions then the mean value is transformed into its logarithm to obtain $X_i$ for each sample.

The values of the characteristic value $X_i$ can be determined experimentally as follows. The properties being measured have been grouped into six blocks as follows:

Group 1; Tensile property

Group 2; Bending property

Group 3; Surface property

Group 4; Shearing property

Group 5; Compressional property

Group 6; Weight and thickness

Tensile Properties

Effective dimension of specimen: Rectangular shape of 5 cm long and 20 cm in width.

Deformation: Tensile deformation is applied along the length direction. And the strain in the width direction becomes approximately zero because of the shape of long sideways of the specimen. This deformation is called "strip biaxial deformation" in mechanics.

Strain rate is kept constant and $4.00 \times 10^{-3}$/sec. After the tensile force attains at $F_m$=500 gf/cm the recovery process is measured.

Characteristic values:

LT; Linearity (unit:non)

WT; Tensile energy per unit area (unit:gf·cm/cm$^2$)

RT; Resilience (unit: %)

These characteristic values are defined by:

$$LT=WT/WOT$$

$$WT=Fd\epsilon (\text{gf·cm/cm}^2) \quad \int_0^{\epsilon m}$$

$$RT=(WT'/WT) \cdot 100$$

where:

$WOT=F_m \epsilon_m/2$

F; Tensile force per unit width. (gf/cm)

$\epsilon$; Tensile strain, note that $\epsilon$ has not % unit be dimensionless quality.

$F_m$ and $\epsilon_m$; Maximum values of F and $\epsilon$ respectively.

W'=F'd$\alpha$ (recovering $\int_0^{\epsilon m}$ energy per unit area)

F'; Tensile force in recovering process. (gf/cm)

Remarks: If the tensile direction is along to warp direction, the characteristic values are identified by suffix 1 and to weft direction by suffix 2, such as $WT_1$, $RT_1$, $WT_2$, $RT_2$, . . . . For submitting these values into the translation formula to obtain the calculated hand value, the mean value of the values of warp and weft directions is used. Recently, em is frequently used, and usually the $\epsilon_{m1}$ and $\epsilon_{m2}$ are shown in the short form such as $\epsilon_1$ and $\epsilon_2$, respectively. There is a relation between them such that, $$\epsilon_m = \frac{2[WT]}{[LT] \cdot F_m}$$

$$= \frac{[WT]}{250[LT]}$$

Bending Property

Effective dimension of specimen: 2.5 cm long and 1 cm in width and this 1 cm width is bent. The longitudinal length of the specimen can be chosen at an appropriate size between 2 cm and 20 cm.

Pure bending occurs between the curvatures K=−2.5 and 2.5 (cm$^{-1}$) with constant rate of curvature change. The rate is 0.50 $(cm^{-1})$/sec. The specimen is put vertically to prevent the effect of gravitational force.

Characteristic values:

B; Bending rigidity per unit length (unit:gf·cm$^2$/cm)

2HB ; Moment of histeresis per unit length (unit: gf·cm/cm)

B is obtained as the slope of the M-K curve where M is the bending moment per unit length of the specimen. Here, we have to define B and 2HB again for the standardization of the measurement. B is defined by the slope between K=0.5 and 1.5 for $B_f$ and K=−1.5 and −1.5 for $B_b$, respectively. $B_f$, $B_b$, $B_1$ and $B_2$ are defined as $B_f$=Value of B for face bending, $B_b$=Value of B for back bending, $B_1$=Value of B for warp bending, and $B_2$=Value of B for weft bending.

Positive and negative curvature can also be defined so that the positive curvature corresponds to the curvature in the case of the face bending and the negative of back-side bending. 2HB means the twice value of HB and can be measured as the hysteresis width. In this case, we define the following: 2HB is taken as the mean value of the hysteresis width in the range of K=0.5 ~−1.5 for $2HB_b$. Thus, we have $2HB_f$ and $2HB_b$ and $2HB_b$. $2HB_1$ and $2HB_2$ are also defined by their suffix. For obtaining the calculated hand value, the mean value of those values corresponding to f1, f2, b1 and b2 is used. Alternatively, depending on which property one is interested in, the values are used separately.

Surface Property

Sample size is taken by 20 cm long and 3.5 cm in width, but this size is an example and the sample size is not specified. But the surface of 2 cm long and 0.5 cm in width is measured effectively. Surface fraction and roughness are measured as follows. The contactor for measurement of surface roughness is made by a steel pianowire of with a diameter of 0.5 mm. The wire is bent into a 5 mm "U-shape" and used under the contact force of 10 g (allowance, ±0.5 g) given by a spring with a spring constant of 25±1 gf/mm. The natural frequency of the system should be more than 30 Hz when the contactor is out of contact. Surface friction can be measured by using multiple contactors. Ten pieces of the same wire as the contactor used for the roughness measurement are piled up and placed on the surface of specimen with the compressional force of 50 gf by a dead weight.

Figure 2A:
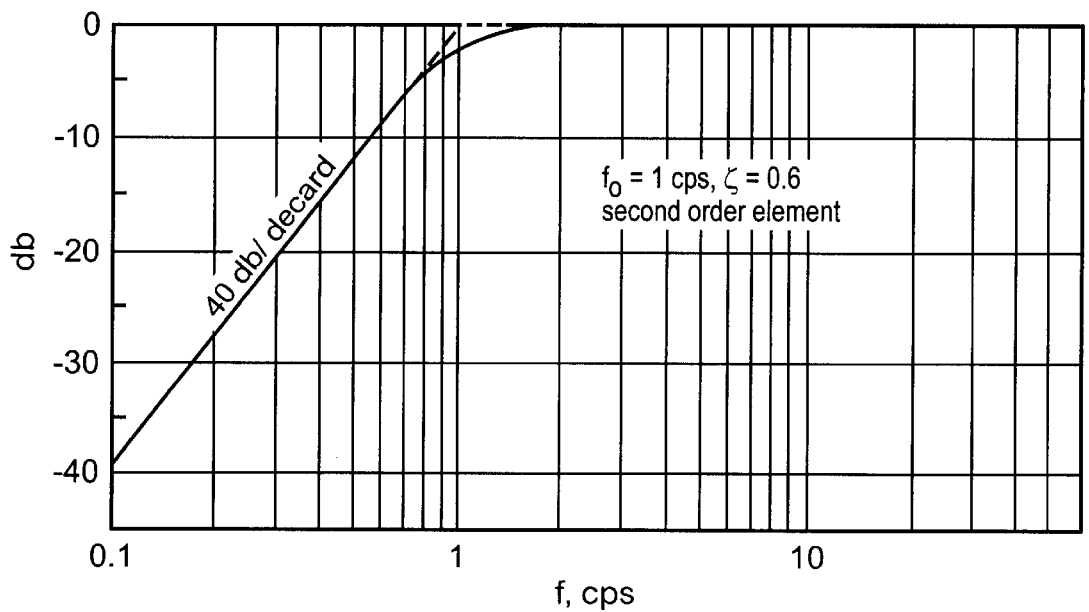
FIG. 2 shows the frequency response of the filter used in the calculation of surface friction and surface roughness.
Figure 2B:
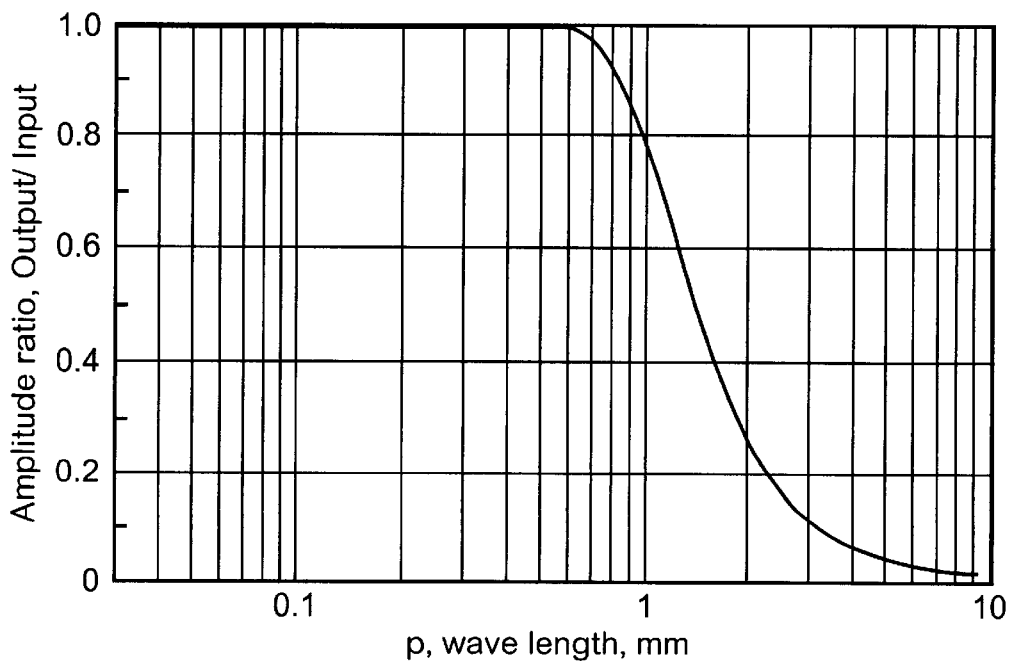

During both roughness and the friction measurement, the specimen is moved between 2 cm interval by a constant velocity of 0.1 cm/sec on a smooth steel plate placed horizontally where the tension of the specimen is kept 20 gf/cm (force per unit length) and the contactor is kept in its position. Both the signal of surface friction and the signal of surface roughness must pass a filter having the frequency response shown in FIG. 2. The transfer function is given by:

$$G(j\omega) = \frac{\omega_n^2}{(j\omega)^2 + 2(j\omega)\zeta\omega_n + \omega_n^2}$$

where $\omega_n$=2πrad/sec, ζ (damping factor)=0.6, and ω is angular frequency. This filter is a high pass filter and the signal with a wave length smaller than 1 mm is allowed to pass Characteristic values:

Frictional measurement:
MIU; mean value of the coefficient of friction (unit: non)
MMD; mean deviation of coefficient of friction (unit: non) Roughness measurement:
SMD; mean deviation of surface roughness (mean deviation of the thickness (unit: micron)

The definitions of MIU, MMD and SMD are, $MIU = 1/X \int_0^x \mu \, dx,$ $MMD = 1/X \int_0^x |\mu - \bar{\mu}| \, dx,$ $SMD = 1/X \int_0^x |T - \bar{T}| \, dx,$ where:

μ; frictional force/compressional force x; displacement of the contactor on the surface of specimen X; 2 cm is taken in this standard measurement T; Thickness of the specimen at position x, the thickness is measured by this contactor.

; Mean value of T  $\bar{T}$

Remarks: MIU, MMD, SMD are also defined for 1 (warp) direction, 2 (weft) direction, face-side and back-side of the specimen. And we identify these values by same way as bending property, for example $MIU_{f1}$, $MIU_{f2}$, $MIU_{b2}$ and etc. For the calculation of hand values the mean value of $MIU_{f1}$ and $MIU_{f2}$ are usually used.

Shearing Property

The size of the specimen is 5 cm×20 cm where 20 cm long side is taken along weft direction.

Constant tension W is applied along the direction orthogonal to the shearing force. This deformation is an overlapped deformation of strip biaxial tensile and shear deformations. The velocity of the shearing is taken as 0.417 mm/sec, and then the rate of shear strain becomes nearly equal to 0.00834/sec.

Characteristic values:

G; Shear stiffness (unit: gf/cm·degree)

2HG; Hysteresis at shear angle φ=0.5 degree. (unit:gf/cm)

2HG5; Hysteresis at φ=5 degree. (unit: gf/cm)

It is noted that G is different from the definition of shear modulus. In this case, G is defined as the (shear force per unit length)/(shear angle). That is, the slope of the F–φ curve is equal to G. As the standard measurement, the slope is measured between φ=0.5° and 5°. In case that the curve is not linear in this region, the mean slope over this region should be taken.

Remarks: In the standard measurement, $G_f$ is measured. The $G_f$ is the value of G when the face of the specimen is front side of the specimen. If we take the shear strain instead of shear angle for defining G, the value is equal to shear modulus and defined by (shear force $F_s$ (gf/cm))/(shear strain=tan φ). The unit becomes (gf/cm), the relation between two values of G defined by tan φ and by φ degree becomes:

G(tan φ)=57.30 G (φdegree)

In the shear deformation of the sample having nonsymmetric weave structure, the Fs-curves are different between positive and negative region. In this case, the measurement of the both region is necessary. And the mean of the values of each regions should be taken as standard measurement for each of G, 2HG and 2HG5.

Compressional Property

Effective dimension of specimen: compressed area is 2 cm$^2$ of a circle. Specimen of 2.5 cm long and 2.0 cm in width is used and the longitudinal direction is taken along either warp or weft direction.

The specimen is compressed by two circular-plates of steel having 2 cm² area. The velocity of the compression is 20 micron/sec and when the pressure attains at 50 g/cm², the recovery process is measured by the same velocity. In case of the measurement of women's thin fabrics, the velocity is reduced to 6.66 micron/sec.

Characteristic values:

LC; Linearity (unit:non)

WC; Energy required for the compression (unit: gf·cm/cm²)

RC; Resilience (unit: %)

The definitions are as follows:

$$LC=WC/WOC$$

$$WC= \int_{T_m}^{T_o} PdT$$

$$RC=WC'/WC$$

where:

T; Thickness of the specimen (cm).

$T_o$; Thickness of the specimen at maximum pressure 0.5 gf/cm², (cm). Note that this value is also used as a characteristic value which expresses sample thickness. In this case, the unit is taken in mm.

$T_m$; Thickness of the specimen at maximum pressure $P_m$ which is:

$P_m$=50 gf/cm²,

WOC;=$P_m (T_o-T_m)/2$

WC'; Recovering energy $\int_{T_m}^{T_o} P^1 dt$ given by the pressure of the recovering process, P' such as WC'=

Thickness and Weight

Thickness is already measured when the compressional property is measured, and T is taken as the thickness when P=0.5 gf/cm² and the unit is taken in mm. Weight is expressed by the weight per unit area of specimen.

Characteristic values:

T; Thickness at pressure 0.5 gf/cm² (unit:mm)

W; Weight per unit area (unit: mg/cm²).

A suitable nonwoven material can be a spunbond material for example of polypropylene or polyethylene fibers. Bicomponent fibers may also be used. The bonding surface of the material should not exceed 15%. Another appropriate nonwoven material is a carded thermobonded material of e g polypropylene, polyester- or bicomponent fibers. The bonding surface should be between 15 and 25%. The basis weight of the nonwoven materials contained in the laminate should be at least 20 g/m², preferably between 20 and 100 g/m² and more preferably between 30 and 60 g/m².

As a carrier material 11 there can be used a plastic film or another suitable material, e.g., a nonwoven. One example of a suitable carrier material is an embossed polypropylene film. The carrier material 11 should be adapted to function as a receiving surface for the tape portions 8,10 or attachment means, at which a plastic film is suitable in case the attachment means are tape members. In case other types of attachment means are used instead of tapes, e.g., hooks of the touch-and-close type, another type of carrier material should be used which may function as a loop material for the attachment means in question.

The carrier material 11 and the soft nonwoven material 12 are preferably glued together. In order to achieve sufficient flexibility and softness the glue amount should not exceed 8 g/m². The gluing technique can be so called strip-coated or full-coated.

Tests have been made with different types of laminates used as belts in incontinence products. It has then been found that laminates having a Shinyakasa value according to Kawabata of 5 or more did not give rise to skin injuries or irritations.

Examples of such belt laminates are:

A: Loosely bonded spunbond of polyethylene, basis weight 40 g/m², glued in strip-coat pattern to a SOPP (simultan oriented polypropylene)-plastic film, 18 μm. Glue amount 3,5 g/m². The Shinyakasa value according to Kawabata was 10,37.

B: The same as A but another type of strip-coat pattern at the gluing. The Shinyakasa-value according to Kawabata was 9,74.

C: Loosely bonded spunbond of polypropylene, basis weight 40 g/m², glued in stripcoat pattern to a SOPP (simultan oriented polypropylene)-plastic film, 18 μm. Glue amount 3,5 g/m². The Shinyakasa value according to Kawabata was 6,88.

D: The same as C but another type of strip-coat pattern at the gluing. The Shinyakasa-value according to Kawabata was 6,22.

E: Thermobonded carded nonwoven of polypropylene, basis weight 30 g/m², glued in full-coat pattern to a SOPP (simultan oriented polypropylene)-plastic film, 18 μm. Glue amount 6 g/m². The Shinyakasa value according to Kawabata was 8,35.

F: The same as E but another gluing technique. The Shinyakasa value according to Kawabata was 8,69.

G: Thermobonded carded nonwoven of polypropylene, basis weight 35 g/m², glued in full-coat pattern to a SOPP (simultan oriented polypropylene)-plastic film, 18 μm. Glue amount 6 g/m². The Shinyakasa value according to Kawabata was 10,22.

H: The same as E but another gluing technique. The Shinyakasa value according to Kawabata was 10,89.

The invention is of course not limited to the above described embodiments but can be modified within the scope of the claims.

What is claimed is:

1. An absorbent article comprising a liquid permeable topsheet, a liquid impermeable backsheet and an absorbent body enclosed therebetween, said article having a front portion, a rear portion and a crotch portion therebetween, and further is provided with a belt attached to or intended to be attached to the rear portion of the article and to the front portion of the article, in such a way that the article will assume a pantlike shape, where the belt forms a part of a waist portion of the article, the belt comprises a flexible laminate of a carrier material intended to form an outside of the belt and a nonwoven material forming an inside of the belt which will be in direct contact with a user, the carrier material and the nonwoven material are glued together with a glue amount of no more than 8 g/m² thus making the flexible laminate soft with a Shinyakasa value according to Kawabata of 5 or more wherein the Shinyakasa value according to Kawabata is determined according to the description set forth in the specification.

2. The absorbent article according to claim 1, wherein said nonwoven material is a spunbond material.

3. The absorbent article according to claim 1, wherein said nonwoven material is a carded material.

4. The absorbent article according to claim 1, wherein the carrier material is of a material suited as a receiving surface for tape members or hook and loop fasteners arranged at the front part of the article.

5. The absorbent article according to claim 1, wherein the carrier material and the nonwoven material are glued together with a glue amount of no more than 8 g/m$^2$.

6. The absorbent article according to claim 1, wherein a basis weight of the nonwoven material is at least 20 g/m$^2$.

7. The absorbent article according to claim 1, wherein the article is a diaper or an incontinence guard.

8. The absorbent article according to claim 6, wherein the basis weight is between 20 and 100 g/m$^2$.

9. The absorbent article according to claim 6, wherein the basis weight is between 30 and 60 g/m$^2$.

* * * * *